(12) United States Patent
Opolski

(10) Patent No.: US 6,238,799 B1
(45) Date of Patent: *May 29, 2001

US006238799B1

(54) ARTICLES PREPARED FROM WATER-BASED HYDROPHILIC COATING COMPOSITIONS

(75) Inventor: Margaret P. Opolski, Carlisle, MA (US)

(73) Assignee: Surface Solutions Laboratories, Inc., Carlisle, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/796,987

(22) Filed: Feb. 7, 1997

Related U.S. Application Data

(60) Provisional application No. 60/011,391, filed on Feb. 9, 1996.

(51) Int. Cl.⁷ .................................................. B32B 27/00
(52) U.S. Cl. .................... 428/423.1; 428/34.3; 428/36.5; 428/411.1; 428/424.2; 428/425.1; 428/423.5; 521/57; 524/500; 524/503; 524/507; 604/265
(58) Field of Search ..................... 524/500, 503, 524/507; 428/423.1, 423.5, 425.1, 424.2, 411.1, 34.3, 36.5; 521/57; 427/222; 604/265

(56) References Cited

U.S. PATENT DOCUMENTS

| | | | |
|---|---|---|---|
| 4,100,309 | 7/1978 | Micklus et al. | 427/2 |
| 4,119,094 | 10/1978 | Micklus et al. | 128/132 R |
| 4,331,783 | 5/1982 | Stoy et al. | 525/294 |
| 4,337,327 | 6/1982 | Stoy et al. | 525/280 |
| 4,369,294 | 1/1983 | Stoy et al. | 525/340 |
| 4,370,451 | 1/1983 | Stoy et al. | 252/294 |
| 4,379,874 | 4/1983 | Stoy et al. | 524/27 |
| 4,420,589 | 12/1983 | Stoy et al. | 525/93 |
| 4,487,808 | 12/1984 | Lambert | 428/423.1 |
| 4,521,551 | 6/1985 | Chang et al. | 523/120 |
| 4,589,873 | 5/1986 | Schwartz et al. | 604/265 |
| 4,642,267 | 2/1987 | Creasy | 525/125 |
| 4,729,914 | 3/1988 | Kliment et al. | 428/36 |
| 4,789,720 | 12/1988 | Teffenhart | 528/76 |
| 4,801,475 | 1/1989 | Halpern et al. | 427/338 |
| 4,810,543 | 3/1989 | Gould et al. | 428/35.7 |
| 4,847,324 | 7/1989 | Creasy | 525/57 |
| 4,876,126 * | 10/1989 | Takemura et al. | 428/35.7 |
| 4,943,460 | 7/1990 | Markle et al. | 428/36.9 |
| 5,001,009 | 3/1991 | Whitbourne | 428/412 |
| 5,026,607 | 6/1991 | Keizulas | 428/423 |
| 5,041,100 | 8/1991 | Rowland et al. | 604/265 |
| 5,066,705 * | 11/1991 | Wickert | 524/457 |
| 5,077,352 | 12/1991 | Elton | 525/409 |
| 5,155,090 * | 10/1992 | Aono et al. | 503/227 |
| 5,157,069 * | 10/1992 | Campbell | 524/500 |
| 5,272,012 | 12/1993 | Opolski | 428/423.1 |
| 5,331,027 | 7/1994 | Whitbourne . | |
| 5,556,429 | 9/1996 | Felt | 623/66 |
| 5,558,900 | 9/1996 | Fan et al. | 427/2.28 |
| 5,582,794 | 12/1996 | Hagiwara et al. . | |
| 5,608,000 * | 3/1997 | Duan et al. | 524/500 |
| 5,620,765 * | 4/1997 | Shaw-Klein et al. | 428/64.1 |
| 5,658,617 * | 8/1997 | Gobel et al. | 524/507 |
| 5,747,166 * | 5/1998 | Schwarte et al. | 428/423.1 |
| 5,753,740 * | 5/1998 | Odawa et al. | 524/414 |
| 5,763,529 * | 6/1998 | Lucas | 524/507 |
| 5,767,188 * | 6/1998 | Kamikuri et al. | 524/507 |
| 5,919,570 | 7/1999 | Hostettler et al. . | |

FOREIGN PATENT DOCUMENTS

| | | |
|---|---|---|
| 0 166 998 | 1/1986 | (EP) . |
| 0483941 | 5/1992 | (EP) . |
| WO93/11751 | 6/1993 | (WO) . |
| WO95/06670 | 3/1995 | (WO) . |

OTHER PUBLICATIONS

Brynda et al. "Polyethylene/hydrophilic polymer blends for biomedical apoplications" *Biomaterials* 8:57 (Jan. 1987).

Y.L. Fan "Hydrophilic Polymers (for Friction Reduction)" appearing in *Polymeric Materials Encyclopedia* J.C. Salomone:Ed. CRC Press, New York 1996 pp. 3107–3115.

\* cited by examiner

*Primary Examiner*—Judy M. Reddick
(74) *Attorney, Agent, or Firm*—Clark & Elbing LLP; Mary Rose Scozzafava

(57) ABSTRACT

A water-based coating composition suitable for preparing hydrophilic surfaces on various articles is provided which includes a supporting polymer having functional moieties capable of undergoing crosslinking reactions, said supporting polymer soluble in or emulsified in an aqueous based medium; and a hydrophilic polymer, said hydrophilic polymer associated with the supporting polymer. The composition is characterized in that, when crosslinked at the functional moieties, the supporting polymer forms a three-dimensional network which substantially minimizes disassociation of the hydrophilic polymer.

14 Claims, No Drawings

ARTICLES PREPARED FROM WATER-BASED HYDROPHILIC COATING COMPOSITIONS

This application claims priority under 35 U.S.C. §5119 (e) from Provisional application No. 60/011,391, which was filed on Feb. 9, 1996 and entitled "Alternative Water-based Hydrophilic Coatings and Articles Prepared Therefrom", which is hereby incorporated in its entirety by reference.

FIELD OF THE INVENTION

The present invention relates to hydrophilic coatings and coated articles derived therefrom. Further, the invention relates to coating composition which can be delivered from an aqueous based formulation.

BACKGROUND OF THE INVENTION

Devices used in the medical and dental industry are prepared from metals, ceramics, or synthetic or natural plastics and are often hydrophobic and non-slippery. Catheters and guide wires which are used for insertion through blood vessels, urethra or other body conduits require low-friction surfaces for preventing injury or inflammation of mucous membranes and for facilitating surgical procedures. To render the device more slippery, the device surfaces are often coated with low-friction materials, such as ptfe, Teflon®, silicone oil, glycerin or silicone fluid. This low-friction coating may result in the loss of maneuverability of the device from outside the body because they are slippery even when dry. Surface modification of hydrophobic, non-biocompatible or non-slippery surfaces by coating with a hydrophilic polymer is known; however, hydrophilic polymer coatings, when hydrated, possesses little in the way of physical integrity because of the high water content.

Prior art references have chemically linked a hydrophilic polymer to a more durable undercoat to improve the physical integrity of the hydrophilic coating. See, Gould in U.S. Pat. No. 4,810,543 and Kliment in U.S. Pat. No. 4,729,914. Baker (U.S. Pat. No. 4,980,231) and Markel (U.S. Pat. No. 4,943,460) describe the coupling of a polyvinylpyrrolidone polymer with an undercoating of an acid functional or anhydride functional material.

The prior art also has attempted to improve wet strength and coating durability while retaining slip by physically blending or co-extruding the hydrophilic polymer with a co-material having greater physical integrity. See, Creasy in U.S. Pat. Nos. 4,642,267 and 4,847,324, in which a polyurethane or a polyvinyl butyral is blended with a poly(N-vinyl lactam). Other references disclose the preparation of interpolymers. See, Micklus (U.S. Pat. Nos. 4,100,309 and 4,119,094) which report an association between polyurethane and polyvinylpyrrolidone polymers. Whitborne in U.S. Pat. No. 5,001,009 describes hydrophilic coatings including a polyolefin such as polyvinylpyrrolidone and a water-insoluble stabilizing polymer, such as cellulose ester. The two polymers may be applied in separate layers or may be premixed and applied in a single step.

Other attempts in the prior art to improve the performance of hydrophilic coatings include use of modified polyurethanes, which possess short hydrophilic segments. See, Teffenhart in U.S. Pat. No. 4,789,720, in which a hydrophilic polyurethane is prepared having polyethylene glycol and polypropylene glycol segments. Stoy et al. in U.S. Pat. Nos. 4,370,451, 4,379,874, 4,420,589, 4,331,783, 4,369,294, 4,337,327 and 4,026,296 describe a series of hydrophilic block copolymers including acrylamides and modified acrylonitriles which have found some use as coatings. These polymers possess limited physical strength when hydrated and are delivered from organic solvents.

Elton in U.S. Pat. No. 5,077,352 describes a cross-linked polyurethane-poly(ethylene oxide) composition which is derived by polymerization of an isocyanate and a polyol in a poly(ethylene oxide) containing solution. The solvent used must not contain any active hydrogens and hence the system may not be applied from aqueous media.

Kiezulas in U.S. Pat. Nos. 5,026,607 and Opolski in 5,272,012 describe water-based, lubricous coatings having domains of a siloxane slip additive within a crosslinked urethane. The slip additives is maintained in distinct domains which replenish the surface of the slip additive as it is removed during use. While retaining good slip, the lubricous surface is non-robust and abrades easily due to the poor compatibility of the siloxane slip additive with the polyurethane and low crosslink density of the urethane. Further, there are health concerns with the retention of siloxane in the body.

In all the above examples, the coatings are either fragile and loosely bound to the substrate or demonstrate limited wet strength. In addition, most of the coating procedures require use of organic solvents, which is discouraged from environmental, cost and worker/patient safety standpoints. Thus, many technical problems directed to providing a durable, low-cost and safe hydrophilic coating remain unresolved.

It is an object of the present invention to provide a coating which is hydrophilic, containing water for anti-adhesion, slip and electrical and ion transport, yet durable—particularly in the water-swollen phase.

It is yet a further object of the invention to provide a coating which is a poor growth medium for microbes.

It is another object of the invention to provide a coating which may be applied from aqueous-based solutions.

These and other objects are provided by the present invention which is described hereinbelow.

SUMMARY OF THE INVENTION

In one aspect of the invention, a water-based coating composition is provided including a supporting polymer comprising a plurality of functional moieties capable of undergoing crosslinking reactions, said supporting polymer soluble in or emulsified in an aqueous based medium; and a hydrophilic polymer, said hydrophilic polymer associated with the supporting polymer. The composition is characterized in that, when crosslinked at the functional moieties, the supporting polymer forms a three-dimensional network which minimizes disassociation of the hydrophilic polymer and maintains the slip of the composition.

The functional moiety may be selected from the group consisting of amino, hydroxyl, amido, carboxylic acid and derivatives thereof, sulfhydryl (SH), unsaturated carbon bond and heteroatom bonds, N—COOH, N(C=O)H S(OR), alkyd/dry resins, formaldehyde condensates, methylol acrylamides and allylic groups. The supporting polymer may be selected from the group consisting of polyacrylates, polymethacrylates, polyurethanes, polyethylene and polypropylene co-difunctional polymers, polyvinyl chlorides, epoxides, polyamides, polyesters and alkyd copolymers. The hydrophilic polymer may be selected from the group consisting of poly(N-vinyl lactams, poly (vinylpyrrolidone), poly(ethylene oxide) polypropylene oxide) polyacrylamides, cellulosics, methyl cellulose, polyanhydrides, polyacrylic acids, polyvinyl alcohols, and polyvinyl ethers.

In one embodiment of the invention, the supporting polymer has a molecular weight in the range of 5,000 to 10,000,000, and preferably has a molecular weight in the range of 30,000 to 100,000. The functional moiety of the supporting polymer has an equivalent weight in the range of about 115 to about 8700. In one embodiment of the invention, the supporting polymer comprises polyacrylate and the equivalent weight of the functional moiety is in the range of about 200 to about 1000. The supporting polymer may comprise polyurethane and the equivalent weight of the functional moiety is in the range of about 1000 to about 8700. The supporting polymer may comprise polyamine epoxide and the equivalent weight of the functional moiety is in the range of about 100 to about 2000.

In other preferred embodiments, the coating composition further comprises a crosslink agent. The crosslink agent may be selected from the group consisting of aziridines, polyfunctional carbodiimides, polyfunctional epoxides, unsaturated carbon and heteroatom bonds, melamine/urea condensates and ionic complexing agents. In other preferred embodiments, the coating composition further comprises one or more additives selected from the group consisting of co-solvents, plasticizers, antifoaming agents, anticrater agents, coalescing solvents, bioactive agents, antimicrobial agents, antithrombogenic agents, antibiotics, pigments, paint additives, radiopacifiers and ion conductors.

In another aspect of the invention, a coated article is provided having a surface coated with a hydrophilic coating. The hydrophilic coating includes a three-dimension supporting polymer matrix, in which the supporting polymer forms a three-dimensional network through crosslinking bridges; and a hydrophilic polymer, in which the hydrophilic polymer is associated with the supporting polymer. The coating is characterized in that the supporting polymer forms a three-dimensional network which, when wet, minimizes eliminates disassociation of the hydrophilic polymer and retains slip for up to 24 hours in ambient aqueous medium.

In one embodiment of the invention, the supporting polymer is selected from the group consisting of polyacrylates, polymethacrylates, polyurethanes, polyethylene and polypropylene copolymers, polyvinyl chlorides, epoxides, polyamides, polyesters and alkyd copolymers. In another embodiment of the invention, the hydrophilic polymer is selected from the group consisting of poly(N-vinyl lactams), poly(vinylpyrrolidone), poly(ethylene oxide) polypropylene oxide) polyacrylamides, cellulosics, methyl cellulose, polyacrylic acids, polyvinyl alcohols, and polyvinyl ethers.

In yet another embodiment of the invention, the crosslinking bridges are selected from the group consisting of moieties of aziridines, carbodiimides, epoxides, unsaturated carbon and heteroatom bonds, ionic complexing agents and melamine/urea condensates. The crosslink density may be in the range of 100–10,000 g/equivalent crosslink.

In yet another preferred embodiment, the article is selected from the group consisting of ocular devices, lenses, medical devices, membranes, recreational products, such as boat hulls, open celled foams, closed celled foams and water-contacting items.

In another aspect of the invention, a method of making a hydrophilic coating is provided which includes applying a coating composition onto a surface of an article. The coating composition comprises a supporting polymer, in which the supporting polymer comprises a plurality of functional moieties capable of undergoing crosslinking reactions and in which the supporting polymer is soluble in or emulsified in an aqueous based solution. The coating composition comprises a hydrophilic polymer, which interacts and is associated with the supporting polymer. The supporting polymer is then crosslinked at the functional moieties so as to form a three-dimensional network which substantially eliminates disassociation of the hydrophilic polymer. The step of crosslinking may be accomplished by initiating a self-crosslinking reaction of the functional moieties of the supporting polymer. Crosslinking is accomplished by addition of a crosslinking agent. In preferred embodiments, the crosslink agent is selected from the group consisting of aziridines, polyfunctional carbodiimides, polyfunctional epoxides, unsaturated carbon and heteroatom bonds, ionic agents and melamine/urea condensates.

In other preferred embodiments, the article surface is pretreated prior to coating. The pretreatment may be selected from the group consisting of chemical etching, corona and plasma etching, priming with other chemicals, coatings and adhesives and mechanical abrasion. In other preferred embodiments, the coated surface is dried to provide a dry coating thereon. In preferred embodiments, the step of coating is accomplished by a technique selected from the group consisting of dip coating, roll coating and spray coating.

By "associated with" as that term is used herein it is meant an interaction of the two polymer (i.e., supporting and hydrophilic) types due to physical entanglement of the supporting polymer and hydrophilic polymer chains as well as other favorable interactions such as hydrogen bonding, van der Waals attraction and ionic attraction.

By "supporting polymer" as that term is used herein it is meant a polymer which is durable in a wet environment and which is capable of favorable or associative interactions with the hydrophilic polymer. The supporting polymer preferable provides a network for containing a hydrophilic polymer. The combination high wet strength and favorable, associative interaction with the hydrophilic polymer serves to "support" the hydrophilic polymer in coating.

The term "coating composition" as that term is used herein is meant to include solutions, dispersions and emulsions.

By "crosslink reaction" as that term is used herein it is meant a reaction which forms covalent bridges or linkages between remote sites on the supporting polymer backbone. The crosslink reaction may occur by self-crosslinking of the functional pendant groups directly or by addition of a crosslinking agent which reacts at the functional group to form the requisite linkage.

DETAILED DESCRIPTION OF THE INVENTION

The present invention provides a durable coating for use in articles, such as medical devices, which becomes slippery and lubricous when wet, e.g., when the article comes in contact with body fluids. Advantageously, the composition may be applied from an aqueous medium to the surfaces of an article to provide a durable, hydrophilic coating. The resulting hydrophilic coating properties, such as durability and slip, are affected by the nature of the supporting polymer and hydrophilic additive and by the crosslink type and density of the polymer coating.

A coating composition for use in coating an article comprises an aqueous mixture of a hydrophilic polymer and a supporting polymer having functional groups capable of undergoing crosslinking reactions. The supporting polymer and hydrophilic polymer are well blended and form an association complex in the aqueous-based medium. The association of the two polymer types may be preserved and maintained by crosslinking the functional moieties of the supporting polymer to form a three dimensional polymer network. The three dimensional network entrains and immobilizes the hydrophilic polymer within the coating to minimize its loss to the environment when wet, without interfering with the hydrophilic properties of the hydrophilic polymer. The retention of the hydrophilic polymer in the polymer coating is qualitatively determined by retention of the slippery feel of the coating when wet and/or when rubbed. This may be denoted as the "retained slip" of the hydrophilic coating.

The hydrophilic polymer may be any polymer which swells in the presence of water to provide a "slippery" or lubricous surface. Exemplary hydrophilic polymers include, but are not limited to, poly(N-vinyl lactams, such as poly (vinylpyrrolidone) (PVP) and the like, poly(ethylene oxide) (PEO), poly(propylene oxide) (PPO), polyacrylamides, cellulosics, such as methyl cellulose and the like, polyacrylic acids, such as acrylic and methacrylic acids and the like, polyvinyl alcohols, and polyvinyl ethers and the like.

The hydrophilic polymer may be of any molecular weight, but it preferably has an average molecular weight in the range of about 50,000 to 5,000,000. The molecular weight of the hydrophilic polymer has an effect on its immobilization within the supporting polymer network. It is contemplated that for hydrophilic polymers of lower molecular weights, e.g., less than about 250,000, the crosslink density of the supporting polymer will be adjusted upward accordingly.

The supporting polymer is selected for its ability to positively interact with the hydrophilic polymer to form an association complex, for its durability and for its ability to form a three-dimensional polymer network. A hydrophilic polymer typically possesses a high ionic content, typically by way of polar bonds, which promotes the polymer's affinity for water. Thus, association complexes are favored when the supporting polymer contains a complementary ionic content. Suitable supporting polymers include, but are not limited to, polyacrylates and polymethacrylates, polyurethanes, polyethylene or polypropylene copolymers, polyvinyl chloride, epoxides, polyamides, polyesters, alkyd or copolymers with rubbers, siloxanes or other polymers.

The supporting polymer may be a homopolymer or copolymers or blends. In one embodiment, the supporting polymer may be a copolymer of polymeric systems having no functional moieties, e.g., polyethylene, with polymers selected to provide the functional moieties of the supporting polymer. In preferred embodiments, copolymers of ethylene and acrylic acid may be used. While not required of the invention, it is contemplated that supporting polymers possessing some degree of branching may be preferred, because such branching will serve to further minimize the disassociation and/or leaching of the hydrophilic polymer from the resultant hydrophilic coating.

The supporting polymer possesses a plurality of functional moieties which are capable of participating in a crosslink reaction. In addition, the functional moieties should be stable in the aqueous environment of the coating composition. The functional moieties may be located along the supporting polymer backbone or they may be located as groups pendant to the supporting polymer backbone.

Suitable functional moieties include, but are not limited to, amino, hydroxyl, amido, carboxylic acid and derivatives thereof, sulfhydryl (SH), unsaturated carbon and heteroatom bonds, e.g. C≅N, C=C and the like, N—COOH, N(C=O) H, S(OR) and the like. The functional moiety is incorporated into the supporting polymer in an amount which will provide, under the curing conditions used, the desired crosslink density in the product hydrophilic coating. The amount of functional moiety in the supporting polymer is designated by equivalent weight (eq. wt.), which is defined as the weight of supporting polymer per one equivalent of functional group in the polymer. Thus, the lower the number, the greater the level of functional moiety in the supporting polymer.

The "desired" level of crosslink density is that which will entrain and substantially immobilize the hydrophilic polymer within the crosslinked network without compromising its functionality, e.g. slip. The level of functional moiety required to accomplish this will of course vary dependent upon the nature of the hydrophilic polymer, supporting polymer and crosslink. However, it has been generally observed in a polyacrylate supporting polymer/PEO or PVP hydrophilic polymer coating composition in which a polyfunctional aziridine is used as the crosslink agent that an equivalent weight of about 1100 is insufficient to provide a durable lubricous coating. In contrast, a similar coating composition having an equivalent weight of about 200–375 satisfactorily immobilizes the hydrophilic polymer to provide a durable hydrophilic coating, even when aged up to one year!

In one embodiment of the invention, the supporting polymer is a copolymer in which one of the copolymers contains the desired functional moiety. By way of example, a commercially available polyurethane maybe prepared by condensation in the presence of organic acid to provide a polyurethane with a desired number of acid functional pendant groups. By way of another example, the supporting polymer may be ethylene copolymerized with acrylic acid (or other unsaturated organic acid) to provide a poly (ethylene-co-acrylate). The copolymer is selected having the appropriate apportionment of the two component polymer so as to provide the desired level of pendant acid functional groups. By way of yet another example, the supporting polymer may be an unsaturated carbon monomer, such as ethylene, copolymerized with a double unsaturated monomer, such as butadiene, allylmethacrylate, ethylene glycol dimethacrylate, or used with conventional alkyd modifier systems containing unsaturated fatty acids, to provide a copolymer having an unsaturated double bond functional group. Many of these polymers are commercially available from WITCO and Spencer Kellogg among others.

The supporting polymer may be an oligomer or polymer having a average molecular weight in the range of 5,000–5,000,000, and preferably in the range of 15,000 to 1,000,000 and more preferably in the range of 30,000 to 100,000. Note that when an epoxy is used as the supporting polymer, the molecular weight may be considerably less than that stated. Epoxy oligomers are cured in situ in the presence of amines to provide the high molecular weight supporting polymers. Likewise, isocyanates dispersable in water may allow for similar reactions with active hydrogen containing compounds.

Polymers have several advantages over the use of monomers. First, it avoids toxic monomers which must be rigorously removed before subsequent use in medical applications. Second, it allows preparation of water-based formulations because the polymer is either soluble in water or may be prepared as a water-based emulsion or dispersion. In addition, there is less control over the nature of the polymer, e.g., molecular weight, degree of branching, etc. before blending and crosslinking.

The ratio of supporting polymer to hydrophilic polymer in the coating composition of the invention is in the range of about 1/10 to about 20/1. Weight ratios of supporting polymer/hydrophilic polymer are preferably in the range of about 1/3 to about 5/1. The solids content of the coating composition may vary widely depending upon the molecular weights of the polymers used and the viscosity of the composition. The coating composition may contain about 2–60% solids. More typically, the coating composition contains about 3–15 wt % solids and preferably about 5–10 wt % solids. Water emulsions are lower viscosity.

The coating composition may additionally include a crosslink agent. Suitable crosslink agent include, but are not limited to, polyfunctional aziridines, polyfunctional carbodiimides and polyfunctional epoxides. Additionally, crosslinking may be initiated by external factors, such as heat and/or uv irradiation, either in place of or in conjunction with a crosslink agent. Where higher temperature may be tolerated, the use of melamine and urea/formaldehyde condensates is possible. Typically, the crosslink agent may be a di- or tri-functional compound; however, it is contemplated as being within the scope of the invention to use polyfunctional crosslink agents having three or more functional groups. It is also contemplated as within the scope of the invention to use ionic components, such as Zn, Ca and Mg, as the crosslink agent.

The coating composition may additionally includes co-solvents and/or other additives to facilitate high quality film formation, such as plasticizers, antifoaming agents, anticrater agents and coalescing solvents. Other suitable additives to the coating composition include, but are not limited to, bioactive agents, antimicrobial agents, antithrombogenic agents, antibiotics, pigments, radiopacifiers and ion conductors. Details concerning the selection and amounts of such ingredients are known to those skilled in the arts.

An unexpected advantage of the coating composition of the present invention is that it also provides a poor environment for microbe growth by virtue of the naturally high pH of the composition. Neutral aqueous solutions of hydrophilic polymers such as PEO or PVP are favorable media for microbe growth. The high pH of the supporting polymer/hydrophilic polymer systems significantly prevents microbes from growing. The coating compositions have a high pH because they are neutralized.

A hydrophilic coating demonstrating superior slip and durability is prepared by combining the supporting polymer and hydrophilic polymer of choice in an aqueous medium. Surfactants and other additives may be added to facilitate mixing and/or dispersion of the two polymers in the aqueous medium. Where it is anticipated that the supporting polymer will be self-crosslinking, preparation of the composition is desirably carried out under conditions for which the crosslink reaction does not occur. In some embodiments, where the crosslink agent is quite reactive to the functional groups of the supporting polymer, it should be added to the coating composition just before the coating operation. In other embodiments, where the crosslink agent is not very reactive, the crosslinking reaction may require initiation by some external trigger, such as heat, irradiation, etc. In these instances, the crosslinking agent may be added to the coating composition and stored together.

The coating composition may be applied to an article using conventional coating techniques, such as dip coating, roll coating, spray coating and the like. In a dip coating process, the article is immersed in a bath containing the coating composition and then removed. A dwelling time, for example, as short as one second and as long as one hour may be used depending of the material of construction, complexity of the device and the desired coating thickness. Typical coating thicknesses are in the range of about 0.0001" to about 0.005" (0.1–5 mil).

The wet coated article may be coated by any conventional method and may be allowed to dry to provide a dry coating. Drying may be accomplished merely by standing at ambient conditions or may be accelerated by heating at mild temperatures, such as 30° C.–100° C. Higher temperature crosslink agents and/or uv initiation may be needed.

Once applied, the hydrophobic coating may be "locked" in place by crosslinking of the supporting polymer to form a three-dimensional network. The crosslink reaction may occur before, during or after the drying step, but most typically occurs during or after the drying step. Crosslink density in the product hydrophilic coating will vary significantly with the nature of the supporting polymer and the crosslink agent, as well as the conditions and duration of curing. Crosslink density may be in the range of 100–1000 g/equivalent crosslink. This figure will be modified in the manner discussed above for the equivalent weight of functional moiety.

The crosslink reaction may be self-initiating so that the functional groups themselves form the crosslink. Suitable functional groups capable of self-crosslinking include, but are not limited to, alkyd oxidatively drying resins, formaldehyde condensates, methyol acrylamides and allylic groups. Such crosslinking may be initiated by application of heat or UV energy, for example. Heating up to 150° C. or more may be used.

In other embodiments, the crosslink reaction may be initiated by addition of a crosslink agent to the coating composition. Such crosslink agent may be added to the coating composition immediately prior to the coating operation. Alternatively, the coated article may be exposed to the crosslink agent after coating, such as, by was of example, swelling of a dry coating in an aqueous solution containing the crosslink agent. Suitable crosslink agent include, but are not limited to, polyfunctional aziridines, polyfunctional carbodiimides and polyfunctional epoxides. Where higher temperature may be tolerated, the use of melamine and urea/formaldehyde condensates is possible. Typically, the crosslink agent is a di- or tri-functional compound; however, it is contemplated as being within the scope of the invention to use polyfunctional crosslink agents having any number of functional groups. The crosslink agent may form one or more crosslinks with the supporting polymer and/or crosslink with adjacent crosslink agent. The crosslink agent may additionally react with active substrate moieties on the substrate surface, especially if the functional groups are generated on the surface by pretreatment of the surface to expose functional groups. This results in a higher crosslink density for the hydrophilic polymer, which may be desirable in some instances, for example, where the hydrophilic polymer is of lower molecular weight, has a poorer affinity for the supporting polymer than desired or where the supporting polymer possesses a low level of functional moieties.

In some embodiments of the invention, the hydrophilic polymer may also be crosslinked to the supporting polymer, thereby covalently anchoring the hydrophilic polymer. However, this may not be appropriate in all instances, as restriction of the mobility of the hydrophilic polymer may adversely affect "slip" or lubricating properties of the coating. It is contemplated that such covalent anchoring of the hydrophilic polymer may be suitable used with hydrophilic polymers having been copolymerized with reactive monomers, such as PVP/RCOOH, PVP or PVOH/ anhydrides or PVP/acetamide.

The coating may be applied to a virtually unlimited variety of substrates. The substrates may be solid, woven or porous. Exemplary substrates include polyether block amides, polyethylene terephthalate, polyetherurethane, polystyrene, natural and synthetic rubbers, silicone rubbers, rubber latex, polyester-polyether copolymers, ethylene methacrylic acid di-and interpolymers containing metal salts, PEEK, PCK, polyethers, polyesters, and other polyurethanes, polyecarbonates, polytetramethylene glycol ether urethane and other organic materials including polyvinyl chloride and other vinyl polymers, polyethylene and the like, as well as blends and alloys of the above. Other substrates include metals, such as stainless steel, nickel, nickel cobalt alloys, titanium, NiTi alloy, tantalum, platinum, gold, silver, and tungsten.

In some embodiments, it is desirable to pretreat the substrate surface to improve adhesion of the hydrophilic coating. Those surface treatments known in the art may be used. Exemplary treatments include, chemical etch, such as acid or base etch, plasma or corona etch and/or application of a primer coat having high affinity for the substrate. Mechanical abrasion may also be used.

The coating of the invention has the ability to adsorb and/or release water soluble materials, to pass ions and to conduct electrical impulse. Thus, the coating may be useful in the electrophysiology field where shoulder or edge influences can be moderated and in the antimicrobial field where migration of ionic species or dissociation of complex ionic species may be enhanced.

Mirrored plastic or glass surfaces fog due to microdroplets of water forming on a hydrophobic surface because the water droplets can not wet the surface. Thus, the coating of the invention may be used for visual barriers and ophthalmic uses, including goggles for skiing, swimming and contact lenses.

The durability of the coating lends itself to uses in which much wear or abrasion is present, yet slip property is required. For example, the coating may be applied to ship hulls, for fuel economy and speed or to skis.

The coating composition may also be blown into hydrophilic foams using conventional techniques, such as incorporation of azides (Expancel, Akzo-Nobel) or swelling encapsulated liquids that blow gas into the composition. Open celled foams may be useful in a number of water or hydrophile absorbing applications, such as a sponge or filtration media or padding of or adhesion to delicate water-containing organisms or tissues.

The present invention is illustrated with reference to the following Examples which are not intended to be limiting of the invention, the full scope of which is set forth in the claims which follow.

Coating. Samples of commercially available polymer resins (supporting) were weighed into tared vials. Water was added to bring all solids to approximately the same level. Crosslink agent was added to stirred resins based upon a stoichiometric theoretic equivalent of crosslinker to one part functional moiety in the resin. The actual crosslink equivalent to functional moiety equivalent varied. The mixture was allowed to stand for at least one hour before coating.

Crosslinked samples were then modified with the hydrophilic polymer by adding predissolved 5% by weight hydrophilic polymer resin in water, added to provide a three part supporting polymer resin to one part hydrophilic polymer coating composition, unless noted otherwise.

Film preparation. A coating applicator blade from Gardner Company of 6 wet mils was used to prepare films on standard bare aluminum and cold-rolled steel (3"×6" panels available from Q-Panel Corporation). Films were heated to dry and cure (i.e., crosslink) the resin/crosslinker composition.

Testing. All films were evaluated visually before testing. The panels were then wet and the contact angle of water on the film surface was noted. Wetting was given a qualitative rating of "good" "moderate" or "poor". Films were evaluated for slip by a human touch test.

Double rub testing, a standard testing for resistance to solvent in the paint industry, was conducted on the films. Under moderate finger pressure and in a cycle time of approximately one second, the fingers were passed over the length of the coated panel. The film was held under running ambient water (the solvent in the current test) for the duration of the rubs. Film slip was then evaluated by human touch.

Ambient temperature overnight soaking was used to test the durability of the coating and their capacity to retain slip.

Static friction values were obtained using a Chatillon Digital Force gauge for tension and compression from Commercial Scale Co. A custom 2"×2" (5 cm×5 cm) 0.93 pound (420 g) cast acrylic block with rounded edges was mounted on the wetted panels and the panel was pulled from below the block at an approximate rate of 12"/min. An average of peak tensions was reported.

EXAMPLE 1

This example describes the preparation of a variety of polyacrylate/poly(ethylene oxide) coating compositions using aziridine as the crosslink agent. This example also describes the formation of a hydrophilic coating therefrom.

An aqueous coating composition was prepared using polyacrylates having various equivalent weights of acid moieties. To a solution containing polyacrylate was added Polyox WSR-205 (polyethylene oxide, MW 600,000, Union Carbide) in a 3/1 ratio to obtain a composition having a total of 10 wt % solids.

A hydrophilic coating was prepared by adding an aziridine crosslink agent (KM-10-1703, Stahl Chemical) at 1.1 times the stoichiometric level (relative to eq. wt. acid) and casting a 6 mil thick layer on bare aluminum. The coating was cured at 160° F. for two hours and allowed to stand at ambient overnight.

The resultant film adhered well to cold-rolled steel, aluminum, polyurethane (Tecoflex, Thermedocs), ether amide copolymer (PEBAX, Elf-Atochem), polyester (Hyrel, DuPont) and corona and plasma treated polyethylene, nylon and polyethylene terephthalate. The wetting properties were tested as described above and the slip of the coating was determined by touch as made, after rub test(s) and standing overnight. The average static resistance was determined as described above. Results are reported in Table 1. The Table suggests that polyacrylates with equivalent weights in the range of 215–329 provide superior slip retention and durability.

TABLE 1

| Sample No. | Polyacrylate (source) | eq. wt. (g/eq) | viscosity (cps) | test conditions | wetting | feel | ave. static resistance (lb.) |
|---|---|---|---|---|---|---|---|
| 3-103A | ASE-60 (Rohm & Haas) | 215 | — | no PEO | poor | plastic | 0.395 |
| 3-103AH | ASE-60 (Rohm & Haas) | 215 | 1215 | fresh cured | good | slick | 0.131 |
| | | | | 30 rubs | good | slick | 0.349 |
| | | | | 100 rubs | good | slick | 0.323 |
| | | | | overnight | good | slick | 0.156 |
| 3-103B | 4983R (Michelman) | 329 | — | no PEO | poor | plastic | 1.382 |
| 3-103BH | 4983R (Michelman) | 329 | 438 | fresh cured | good | slick | 0.298 |
| | | | | 30 rubs | good | slick | 0.512 |
| | | | | 100 rubs | good | slick | 0.434 |
| | | | | overnight | good | slick | 0.372 |
| | | | | aged 4 mo | good | slick | 0.235 |
| | | | | aged 1 yr | good | slick | .299 |
| 3-103C | A-5102 (Zeneca) | 1002 | — | no PEO | poor | plastic | 0.733 |
| 3-103CH | A-5102 (Zeneca) | 1002 | 400 | fresh cured | good | slick | 0.12 |
| | | | | 30 rubs | film dissolves | | — |
| 3-103D | A-5090 (Zeneca) | 4675 | — | no PEO | poor | plastic | 0.782 |
| 3-103DH | A-5090 (Zeneca) | 4675 | 240 | fresh cured | good | slick | 0.287 |
| | | | | 30 rubs | film softens and tears | | — |

EXAMPLE 2

This example describes the preparation of a variety of polyacrylate/poly(vinylpyrrolidone) coating compositions using melamine formaldehyde as the crosslink agent. This example also describes the formation of a hydrophilic coating therefrom.

An aqueous coating composition was prepared using polyacrylates having various equivalent weights of acid moieties. To a solution containing polyacrylate was added PVP Povidone K-90 (poly(vinylpyrrolidone), MW 1,000,000, ISP Chemical) in a 3/1 ratio to obtain a composition having a total of 10 wt % solids.

A hydrophilic coating was prepared by adding an melamine formaldehyde crosslink agent (hexamethoxy melamine/formaldehyde, Cymel 303, Cytec Corp.) at 2.0 times the stoichiometric level (relative to eq. wt. acid). The stoichiometric calculations were based upon a functionality of three rather than six for the hexamethoxymelamine, assuming that steric hindrance and lack of availability of reactive acid functionalities for all crosslink functional sites would prevent all six sites from reacting. The coating was cast in a 6 mil thick layer on bare aluminum and was cured at 325° F. for fifteen minutes.

The resultant film adhered well to cold-rolled steel, aluminum, polyurethane (Tecoflex, Thermedocs), ether amide copolymer (PEBAX, Elf-Atochem), polyester (Hyrel, DuPont) and corona and plasma treated polyethylene and polyethylene terephthalate. The wetting properties were tested as described above and the slip of the coating was determined by touch as made, after rub test(s) and standing overnight. The average static resistance was determined as described above. Results are reported in Table 2. It is possible to overcure or over crosslink with melamines because of the multifunctionality of the agent as discussed above. The results of Table 2 suggest that the films formed at lower polymer molecular weights and higher functional group equivalent weight are not durable. Note that samples 3-103CMH and 3-103DMH both scratched in the static resistance test. Use of melamine crosslink in the system produced coatings of acceptable slip and durability using equivalent weights of 215 and 329.

TABLE 2

| Sample No. | Polyacrylate (source) | eq. wt. (g/eq) | test conditions | wetting | feel | ave. static resistance (lb.) |
|---|---|---|---|---|---|---|
| 3-103AM | ASE-60 (Rohm & Haas) | 215 | no PVP | poor | plastic | 0.261 |
| 3-103AMH | ASE-60 (Rohm & Haas) | 215 | fresh cured | good | slick | 0.287 |
| 3-103BM | 4983R (Michelman) | 329 | no PVP | poor | plastic | 0.37 |
| 3-103BMH | 4983R (Michelman) | 329 | fresh cured | moderate | fair | 0.195 |
| | | | 100 rubs | moderate | fair | 0.225 |
| 3-103CM | A-5102 (Zeneca) | 1002 | no PVP | poor | plastic | 0.465 |
| 3-103CMH | A-5102 (Zeneca) | 1002 | fresh cured | good | slick | 0.07 |
| | | | 30 rubs | good | slick | scratches |
| 3-103DM | A-5090 Zeneca) | 4675 | no PVP | poor | plastic | 0.463 |
| 3-103DMH | A-5090 Zeneca) | 4675 | fresh cured | good | slick | 0.125 |
| | | | 30 rubs | good | slick | scratches |

EXAMPLE 3

This example describes the preparation of a variety of polyurethane/poly(ethylene oxide) coating compositions using an aziridine crosslink agent. This example also describes the formation of a hydrophilic coating therefrom.

An aqueous coating composition was prepared using polyurethanes having various equivalent weights of acid. All water based urethane contain some hydrophobic or acidic component. Urethane containing different acid levels are commercially available. To a solution containing polyurethane was added Polyox WSR-205 (polyethylene oxide, MW 600,000, Union Carbide Corporation) in a 3/1 ratio to obtain a composition having a total of 10 wt % solids.

A hydrophilic coating was prepared by adding an aziridine crosslink agent (KM-10-1703, Stahl Chemical) at 1.1 times the stoichiometric level (relative to eq. wt. acid) and casting a 6 mil thick layer on bare aluminum. The coating was cured at 160° F. for two hours and allowed to stand at ambient overnight.

The film adhered well to cold-rolled steel, aluminum, polyurethane (Tecoflex, Thermedocs), ether amide copolymer (PEBAX, Elf-Atochem), polyester (Hyrel, DuPont) and corona and plasma treated polyethylene and polyethylene terephthalate. The wetting properties were tested as described above and the slip of the coating was determined by touch as made, after rub test(s) and standing overnight. The average static resistance was determined as described above. Results are reported in Table 3. The results shown in Table 3 also indicate that there is a point at which the hydrophilic coating loses its combined advantageous slip and durability. Polyurethane systems having an equivalent weight of 1753 and 2805 provided both durability and slip over time. However, with increasing equivalent weight (corresponding to decreasing crosslink density in the product hydrophilic coating), the film loses strength and durability. Films having an equivalent weight of 4315 are borderline acceptable.

TABLE 3

| Sample No. | poly-urethane (source) | eq. wt. (g/eq) | vis-cosity (cps) | test conditions | wet-ting | feel | ave. static resistance (lb.) |
|---|---|---|---|---|---|---|---|
| 3-106A | R-9603 (Zeneca) | 1753 | 734 | fresh cured | good | slick | 0.168 |
| | | | | 30 rubs | good | slick | 0.259 |
| | | | | 100 rubs | good | slick | 0.317 |
| | | | | overnight | good | slick | 0.311 |
| 3-106D | R-9621 (Zeneca) | 2805 | — | fresh cured | good | slick | 0.052 |
| | | | | 30 rubs | good | slick | 0.080 |
| | | | | 100 rubs | good | slick | 0.173 |
| 3-106B | R972 (Zeneca) | 4315 | 706 | fresh cured | good | slick | 0.181 |
| | | | | 30 rubs | good | slick | 0.311 |
| | | | | 100 rubs | good | slick | 0.316 |
| | | | | overnight | moderate | slick | 0.301 |
| 3-C | XW121 (Bayer) | 8630 | 706 | fresh cured | good | slick | 0.197 |
| | | | | 30 rubs | good | slick | 0.435 |
| | | | | 100 rubs | good | slick | 0.576 film tore |

EXAMPLE 4

This example describes the preparation of a variety of polyurethane/poly(vinylpyrrolidone) coating compositions using a melamine formaldehyde crosslink agent. This example also describes the formation of a hydrophilic coating therefrom.

An aqueous coating composition was prepared using polyurethanes having various equivalent weights. To a solution containing polyurethane was added Plasdone K-90 (poly(vinylpyrrolidone), MW 1,000,000, ISP Chemical) in a 1/3 ratio to obtain a composition having a total of 10 wt % solids.

A hydrophilic coating was prepared by adding an melamine formaldehyde crosslink agent (hexamethoxy melamine/formaldehyde, Cymel 303, Cytec Corp.) at 2.0 times the stoichiometric level (relative to eq. wt. acid). The stoichiometric calculations were based upon a functionality of three rather than six for the hexamethoxymelamine, assuming that steric hindrance and lack of availability of reactive acid functionalities for all crosslink functionalities would prevent all six sites from reacting. The coating was cast in a 6 wet mil thick layer on bare aluminum and was cured at 325° F. for 15 minutes.

The film adhered well to cold-rolled steel, aluminum, polyurethane (Tecoflex, Thermedocs), ether amide copolymer (PEBAX, Elf-Atochem), polyester (Hyrel, DuPont) and corona and plasma treated nylon, polyethylene and polyethylene terephthalate. The wetting properties were tested as described above and the slip of the coating was determined by touch as made, after rub test(s) and standing overnight. The average static resistance was determined as described above. Results are reported in Table 4. The results are consistent with the previous examples, that is, even in samples which demonstrate retained slip, there is a point at which durability suffers.

TABLE 4

| Sample No. | poly-urethane (source) | eq. wt. (g/eq) | test conditions | wetting | feel | ave. static resistance (lb.) |
|---|---|---|---|---|---|---|
| 3-119A | R-9603 (Zeneca) | 1753 | fresh cured | good | slick | 0.02 |
| | | | 30 rubs | good | slick | 0.011 |
| | | | 100 rubs | good | slick | 0.004 |
| 3-119B | R-972 (Zeneca) | 4315 | fresh cured | good | slick | 0.033 |
| | | | 30 rubs | good | slick | 0.011 |
| | | | 100 rubs | good | slick | film tore |
| 3-119C | XW-121 (Bayer) | 8630 | fresh cured | good | slick | 0.011 |
| | | | 30 rubs | good | slick | 0.025 |
| | | | 100 rubs | good | slick | film tore |

EXAMPLE 5

This example describes the preparation of a variety of polyurethane/poly(vinylpyrollidone) coating compositions using an epoxy crosslink agent. This example also describes the formation of a hydrophilic coating therefrom.

An aqueous coating composition was prepared using polyurethanes having various equivalent weights. To a solution containing polyurethane was added Plasdone K-90 (poly(vinylpyrrolidone), MW 1,000,000, ISP Chemical) in a 3/1 ratio to obtain a composition having a total of 10 wt % solids.

A hydrophilic coating was prepared by adding an epoxy crosslink agent (Waterpoxy 1401, Hankel Corp.) at 1.0 times the stoichiometric level (relative to eq. wt. functionality). The coating was cast in a 6 wet mil thick layer on bare aluminum and coating was cured at 200° F. for 30 minutes.

The film adhered well to cold-rolled steel, aluminum, polyurethane (Tecoflex, Thermedocs), ether amide copolymer (PEBAX, Elf-Atochem), polyester (Hyrel, DuPont) and corona and plasma treated nylon, polyethylene and polyethylene terephthalate. The wetting properties were tested as described above and the slip of the coating was determined by touch as made, after rub test(s) and standing overnight. The average static resistance was determined as described above. Results are reported in Table 5. The results are consistent with the previous examples, that is, even in samples which demonstrate retained slip, there is a point at which durability suffers.

TABLE 5

| Sample No. | poly-urethane (source) | eq. wt. (g/eq) | test conditions | wetting | feel | ave. static resistance (lb.) |
|---|---|---|---|---|---|---|
| 3-115A | R-9603 (Zeneca) | 1753 | fresh cured | good | slick | 0.152 |
| | | | 30 rubs | good | slick | 0.128 |
| | | | 100 rubs | good | slick | 0.127 |
| 3-115B | R-972 (Zeneca) | 4315 | fresh cured | good | slick | 0.139 |
| | | | 30 rubs | good | slick | 0.232 |
| | | | 100 rubs | good | slick | film tore |
| 3-115C | XW-121 (Bayer) | 8630 | fresh cured | good | slick | 0.095 |
| | | | 30 rubs | good | slick | film tore |

EXAMPLE 6

This example describes the preparation of a variety of epoxide/polyethylene oxide coating compositions using a polyamine as crosslink agent. This example also describes the formation of a hydrophilic coating therefrom.

To a solution containing a polyamine was added Polyox WSR-205 (polyethylene oxide, MW 600,000, Union Carbide) in to obtain a composition having a total of 10 wt % solids.

A hydrophilic coating was prepared by adding an epoxy crosslink agent (Waterpoxy 1401, Hankel Corp.) at 1.0 times the stoichiometric level (relative to eq. wt. functionality of the polyamine). The coating was cast in a 6 wet mil thick layer on bare aluminum and coating was cured at 200° F. for 30 minutes.

The film adhered well to cold-rolled steel, aluminum, polyurethane (Tecoflex, Thermedocs), ether amide copolymer (PEBAX, Elf-Atochem), polyester (Hyrel, DuPont) and corona and plasma treated nylon, polyethylene and polyethylene terephthalate. The wetting properties were tested as described above and the slip of the coating was determined by touch as made, after rub test(s) and standing overnight. The average static resistance was determined as described above. Results are reported in Table 6. The results are consistent with the previous examples, that is, even in samples which demonstrate retained slip, there is a point at which durability suffers.

TABLE 6

| Sample No. | polyamine | eq. wt. (g/eq.) | test conditions | wetting | feel | ave. static resistance (lb.) |
|---|---|---|---|---|---|---|
| 3-114A | Henkel 701 | 162 | fresh cured | good | slick | 0.194 |
| | | | 30 rubs | good | slick | 0.442 |
| 3-114B | Jeffamine D-230 | 115 | fresh cured | good | slick | 0.185 |
| | | | 30 rubs | good | slick | 0.213 |
| 3-114C | Jeffamine CT-3000 | 1000 (branch) | fresh cured | good | slick | 0.11; film dissolved |
| 3-114D | Jeffamine (D-2000) | 1000 (linear) | fresh cured | good | slick | 0.095 |
| | | | 30 rubs | good | slick | film tore |

What is claimed is:

1. A coated article, comprising:
    an article having a hydrophilic coating thereon, said coating comprising:
        a polyurethane polymer matrix, said polyurethane polymer having an equivalent weight of functional moiety pendant to the polyurethane backbone in the range of about 1000 to 2805 g/eq. and forming a three-dimensional network, said network consisting essentially of said polyurethane backbone and crosslinking bridges at said pendent functional moiety; and
        a hydrophilic polymer, said hydrophilic polymer associated with said polyurethane polymer matrix,
        the polyurethane polymer matrix having a crosslink density such that the coating retains slip for up to 24 hours in ambient aqueous medium.

2. The coated article of claim 1, wherein the hydrophilic polymer is selected from the group consisting of poly (vinylpyrrolidone), poly(ethylene oxide), poly(propylene oxide), polyacrylamide, methyl cellulose, polyacrylic acids, polyvinyl alcohols, and polyvinyl ethers.

3. The coated article of claim 1, wherein the crosslinking bridges are selected from the group consisting of moieties derived from aziridine, carbodiimide, epoxides, unsaturated carbon-carbon and carbon-heteroatom bonds, ionic Zn, Ca and Mg, and melamine/urea condensates.

4. The coated article of claim 1, wherein the functional moiety is selected from the group consisting of amino, hydroxyl, amido, carboxylic acid, sulfhydryl, unsaturated carbon-carbon and carbon-heteroatom bonds.

5. The coated article of claim 1, wherein the crosslink density is in the range of 100–10,000 g/equivalent crosslink.

6. The coated article of claim 1, wherein the crosslink density is in the range of 100–1000 g/equivalent crosslink.

7. The coated article of claim 1, wherein the polymer of said polymer matrix has a weight average molecular weight in the range of 5,000 to 10,000,000.

8. The coated article of claim 1, wherein the polymer of said polymer matrix has a weight average molecular weight in the range of 30,000 to 100,000.

9. The coated article of claim 1, wherein the polymer of the polymer matrix and the hydrophilic polymer are present in a ratio in the range of 1:10 to 20:1.

10. The coated article of claim 1, wherein the polymer of the polymer matrix and the hydrophilic polymer are present in a ratio in the range of 1:3 to 5:1.

11. The coated article of claim 1, further comprising:
    one or more additives selected from the group consisting of co-solvents, plasticizers, anti-foaming agents, anti-crater agents, coalescing solvents, bioactive agents, antimicrobial agents, antithrombogenic agents, antibiotics, pigments, paint additives, radiopacifiers and ion conductors.

12. A coated medical device, comprising:
    a medical device having a surface coated with a hydrophilic coating, said hydrophilic coating comprising:
        a three-dimensional polyurethane polymer matrix, said polyurethane polymer having an equivalent weight of functional moiety pendant to the polyurethane backbone of about 1000 to 2805 g/eq. and forming a three-dimensional network, said network consisting essentially of said polyurethane backbone and crosslinking bridges at said pendent functional moiety; and
        a poly(vinylpyrrolidone) hydrophilic polymer, said poly(vinylpyrrolidone) polymer associated with said polyurethane polymer,
        the polyurethane polymer matrix having a crosslink density such that the coating retains slip for up to 24 hours in ambient aqueous medium.

13. The coated article of claim 1, wherein said functional pendant moiety comprises an organic acid moiety.

14. The coated article of claim 1, wherein said polyurethane backbone comprises a condensation product with an organic acid, wherein said organic acid provides said acid functional moiety.

* * * * *